United States Patent
Bertz et al.

(10) Patent No.: US 7,132,097 B2
(45) Date of Patent: *Nov. 7, 2006

(54) SUNSCREEN COMPOSITIONS

(75) Inventors: Steven H. Bertz, Morristown, NJ (US); Steven A. Orofino, Hamburg, NJ (US); Mihaela Gorcea, North Bergen, NJ (US)

(73) Assignee: ISP Investments Inc., Wilmington, DE (US)

( * ) Notice: Subject to any disclaimer, the term of this patent is extended or adjusted under 35 U.S.C. 154(b) by 98 days.

This patent is subject to a terminal disclaimer.

(21) Appl. No.: 10/961,564

(22) Filed: Oct. 8, 2004

(65) Prior Publication Data

US 2006/0078514 A1   Apr. 13, 2006

(51) Int. Cl.
*A61Q 19/04* (2006.01)
*A61Q 19/00* (2006.01)
*A61K 8/02* (2006.01)
*A61K 8/00* (2006.01)
*A61K 8/06* (2006.01)

(52) U.S. Cl. .......... 424/59; 424/60; 424/400; 424/401; 514/937; 514/938

(58) Field of Classification Search ......... 424/59, 424/60, 400, 401; 514/937, 938
See application file for complete search history.

(56) References Cited

U.S. PATENT DOCUMENTS 5,510,120 A * 4/1996 Jones et al. ............... 424/499
6,593,476 B1 * 7/2003 Heywang et al. ......... 548/310.7

* cited by examiner

*Primary Examiner*—Shelley A. Dodson
(74) *Attorney, Agent, or Firm*—William J. Davis; Walter Katz

(57) ABSTRACT

A sunscreen composition which includes at least one UV-B active ingredient therein, optionally with a UV-A active, and a phenylethyl or benzyl ester in an amount sufficient to boost the SPF rating of the UV-B active therein.

6 Claims, No Drawings

SUNSCREEN COMPOSITIONS

CROSS REFERENCE TO RELATED APPLICATIONS

This application is related to co-pending U.S. application Ser. No. 10/859,533, filed Jun. 2, 2004, which is a continuation-in-part of co-pending U.S. application Ser. No. 10/617,493, filed Jul. 11, 2003, the entire contents of which are incorporated by reference herein.

BACKGROUND OF THE INVENTION

1. Field of the Invention

This invention relates to sunscreen compositions, and, more particularly, to such compositions containing an additive ingredient to boost the SPF rating of a UV-B active therein.

2. Description of the Prior Art

Sunscreen compositions generally contain an active ingredient to absorb UV-B irradiation of wavelengths from 280 to 320 nm, which can cause erythema burning of the skin. Such compositions also may contain actives that absorb UV-A irradiation of wavelengths from 320 to 400 nm. These agents protect sensitive skin from harmful effects. These active sunscreen compounds (and the active amounts thereof) generally are selected to provide a desired sun protection factor (SPF). This SPF rating is expressed mathematically by the ratio of the irradiation time required to attain the erythema-forming threshold with the UV screening agent present to the time required to attain the same threshold in the absence of the UV screening agent.

An active sunscreen agent which absorbs irradiation in the UV-B range generally contributes much of the SPF rating to a sunscreen composition. Thus, high SPF values ordinarily are obtained by incorporating a large amount of a UV-B absorbing sunscreen compound therein, e.g., octylmethoxy cinnamate and benzophenone-3. However, addition of such compounds in such large quantities can cause skin irritancy as well as increase the cost of the formulation.

Accordingly, it is an object of this invention to provide a sunscreen composition which includes an additive ingredient which boosts the SPF rating of the composition.

Another object herein is to provide sunscreen compositions which require less UV-B compound to achieve a desired SPF rating for the composition Still another object of this invention to provide a sunscreen composition including a phenylethyl or benzyl ester compound which boosts the SPF rating of the composition.

SUMMARY OF THE INVENTION

What is described herein are sunscreen compositions which include a UV-B active whose SPF rating is boosted by the presence in the composition of a phenylethyl, benzyl or substituted benzyl ester, which are arylcarboxylic esters of 2-phenylethyl alcohol, 1-phenylethyl alcohol, benzyl alcohol or substituted benzyl alcohol. Representative esters include 2-phenylethyl benzoate, 2-phenylethyl toluate, di-2-phenylethyl phthalate, 1-phenylethylbenzoate, benzylbenzoate and substituted benzylbenzoate.

DETAILED DESCRIPTION OF THE INVENTION

The sunscreens which may be formulated according to the present invention typically comprise chemical absorbers, but may also comprise physical blockers. Exemplary sunscreens which may be formulated into the compositions of the present invention are chemical absorbers such as p-aminobenzoic acid derivatives, anthranilates, benzophenones, camphor derivatives, cinnamic derivatives, dibenzoyl methanes, β,β-diphenylacrylate derivatives, salicylic derivatives, triazine derivatives, benzimidazole compounds, bis-benzoazolyl derivatives, methylene bis-(hydroxyphenylbenzotriazole) compounds, the sunscreen polymers and silicones, or mixtures thereof. These are variously described in U.S. Pat. Nos. 2,463,264, 4,367,390, 5,166,355 and 5,237,071 and in EP-0,863,145, EP-0,517,104, EP-0,570,838, EP-0,796,851, EP-0,775,698, EP-0,878,469, EP-0-933,376, EP-0,893,119, EP-0,669,323, GB-2,303,549, DE-1,972,184 and WO-93/04665, also expressly incorporated by reference. Also exemplary of the sunscreens which may be formulated into the compositions of this invention are physical blockers such as cerium oxides, chromium oxides, cobalt oxides, iron oxides, red petrolatum, silicone-treated titanium dioxide, titanium dioxide, zinc oxide, and zirconium oxide, or mixtures thereof.

A wide variety of sunscreens is described in U.S. Pat. No. 5,087,445, issued to Haffey et al. on Feb. 11, 1992; U.S. Pat. No. 5,073,372, issued to Turner et al. on Dec. 17, 1991; and Chapter VIII of *Cosmetics, Science and Technology* by Segarin et al., pages 189 et seq. (1957), all of which are incorporated herein by reference in their entirety.

Preferred among those sunscreens which may be formulated into the compositions of the instant invention are those selected from among: aminobenzoic acid, amyldimethyl PABA, cinoxate, diethanolamine p-methoxycinnamate, digalloyl trioleate, dioxybenzone, 2-ethoxyethyl p-methoxycinnamate, ethyl 4-bis(hydroxypropyl)aminobenzoate, 2-ethylhexyl-2-cyano-3,3-diphenylacrylate, ethylhexyl p-methoxycinnamate, 2-ethylhexyl salicylate, glyceryl aminobenzoate, homomenthyl salicylate, homosalate, 3-imidazol-4-ylacrylic acid and ethyl ester, methyl anthranilate, octyldimethyl PABA, 2-phenylbenzimidazole-5-sulfonic acid and salts, red petrolatum, sulisobenzone, titanium dioxide, triethanolamine salicylate, N,N,N-trimethyl-4-(2-oxoborn-3-ylidene methyl)anillinium methyl sulfate, and mixtures thereof.

Similarly preferred sunscreens active in the UV-A and/or UV-B range include:
p-aminobenzoic acid,
polyoxyethylene p-aminobenzoate,
2-ethylhexyl p-dimethylaminobenzoate,
ethyl N-oxypropylene p-aminobenzoate,
glycerol p-aminobenzoate,
4-isopropylbenzyl salicylate,
2-ethylhexyl 4-methoxycinnamate,
methyl diisopropylcinnamate,
isoamyl 4-methoxycinnamate,
diethanolamine 4-methoxycinnamate,
3-(4'-trimethylammonium)-benzyliden-bornan-2-one methylsulfate,
2-hydroxy-4-methoxybenzophenone,
2-hydroxy-4-methoxybenzophenone-5-sulfonate,
2,4-dihydroxybenzophenone,
2,2',4,4'-tetrahydroxybenzophenone,
2,2'-dihydroxy-4,4'-dimethoxybenzophenone,
2-hydroxy-4-n-octyloxybenzophenone,
2-hydroxy-4-methoxy-4'-methoxybenzophenone,
α-(2-oxoborn-3-ylidene)-tolyl-4-sulfonic acid and soluble salts,
3-(4'-sulfo)benzyliden-bornan-2-one and soluble salts,
3-(4'methylbenzylidene)-d,l-camphor, 3-benzylidene-d,l-camphor,
benzene 1,4-butanediol-di(3-methylidene-10-camphosulfonic) acid and salts thereof,
terephthalylidene-3,3'-dicamphor-10,10'-disulfonic acid
2,4,6-tris[p-(2'-ethylhexyl-1'-oxycarbonyl)-anilino]-1,3,5-triazine,
2-[(p-(tert-butylamido)anilino]-4,6-bis-[(p-(2'-ethylhexyl-1'-oxycarbonyl)aniline]-1,2,5-triazine,
2,4-bis{[4-(2-ethylhexyloxy)]-2-hydroxy]-phenyl}-6-(4-methoxyphenyl)-1,3,5-triazine ("TINOSORB S", marketed by Ciba),
the polymer of N-(2 and 4)-[(2-oxoborn-3-yliden)methyl]benzyl]-acrylamide,
1,4 butanediol-bisbenzimidazolyl-phenylen-3,3',5,5'-tetrasulfonic acid and salts thereof,
the benzalmalonate-substituted polyorganosiloxanes,
the benzotriazole-substituted polyorganosiloxanes (e.g., Drometrizole Trisiloxane),
dispersed 2,2'-methylene-bis-[6-(2H-benzotriazol-2-yl)-4-(1,1,3,3-tetramethylbutyl)phenol] such as that marketed under the trademark MIXXIM BB/100 by Fairmount Chemical, or micronized in dispersed form thereof such as that marketed under the trademark "TINOSORB M" by Ciba-Geigy, and solubilized 2,2'-methylene-bis-[6-(2H-benzotriazol-2-yl)-4-(methyl)phenol] such as that marketed under the trademark "MIXXIM BB/200" by Fairmount Chemical.

Typically preferred among the subject sunscreens are one or more of the following: octyl salicylate, octocrylene, and oxybenzone. Combinations of one or more of these sunscreens are similarly preferred.

The dibenzoyl methane derivatives other than avobenzone are also preferred sunscreens according to the present invention. These are described, for example, in FR-2,326,405, FR-2,440,933 and EP-0,114,607, hereby expressly incorporated by reference.

More preferred dibenzoyl methane sunscreens include (whether singly or in any combination):
2-methyldibenzoylmethane
4-methyldibenzoylmethane
4-isopropyldibenzoylmethane
4-tert-butyldibenzoylmethane
2,4-dimethyldibenzoylmethane
2,5-dimethyldibenzoylmethane
4,4'-diisopropyldibenzoylmethane
4,4'-dimethoxydibenzoylmethane
2-methyl-5-isopropyl-4'-methoxydibenzoylmethane
2-methyl-5-tert-butyl-4'-methoxydibenzoylmethane
2,4-dimethyl-4'-methoxydibenzoylmethane
2,6-dimethyl-4-tert-butyl-4'-methoxydibenzoylmethane At least one of the subject UV-A and/or UV-B sunscreens is advantageously formulated into the compositions of the invention in amounts ranging from about 0.1% to about 10%, and preferably from about 1% to about 6%, by weight thereof. Of course, depending upon the nature of the particular formulation, higher or lower amounts may be suitable.

The compositions of the present invention can be formulated into a wide variety of product types, including creams, dispersions, emulsions (e.g., oil-in-water, water-in-oil, water-in-oil-in-water, and oil-in-water-in-silicone), gels, ointments, lotions, milks, mousses, sprays, tonics, and the like.

The topical cosmetic compositions of the present invention typically comprise a carrier (vehicle or diluent) or mixture of carriers. The carrier should be cosmetically and/or pharmaceutically acceptable, which reflects that the carrier is suitable for topical application onto the skin, has good aesthetic properties, is compatible with the copolymer of the present invention, and any other components, and will not cause any untoward safety or toxicity concerns. The carriers and additional components used to formulate such products vary with the product type and may be routinely chosen by one skilled in the art. The following is a description of some of these carriers and additional components.

The compositions of the present invention can comprise a carrier, or a mixture of carriers, suitable for topical application onto the human skin. The carriers typically constitute from about 0.5% to about 99.5% by weight, preferably from about 5.0% to about 99.5% by weight, more preferably from about 10.0% to about 98.0% by weight, of the composition. As used herein, the phrase "suitable for topical application onto human skin" reflects that the carrier does not damage or negatively affect the aesthetics of, or cause irritation to, human skin.

Carriers suitable for use with the present invention include, for example, those used in the formulation of a wide variety of product types, including creams, dispersions, emulsions, gels, lotions, milks, mousses, sprays, and tonics.

The carriers used herein can include a wide range of components conventionally used in cosmetic/dermatological compositions. The carriers can contain a solvent to dissolve or disperse the polymer. The carriers can also contain a wide variety of additional materials including, but not limited to, esters (such as isopropyl myristate), halogenated hydrocarbons (such as freons), hydrocarbons (such as decene, hexane, and isobutene), linalool, and volatile silicon derivatives (especially siloxanes such as phenyl pentamethyl disiloxane, methoxypropyl heptamethyl cyclotetrasiloxane, chloropropyl pentamethyl disiloxane, hydroxypropyl pentamethyl disiloxane, octamethyl cyclotetrasiloxane, decamethyl cyclopentasiloxane, cyclomethicone, dimethicone), and mixtures thereof.

Mousses and aerosol sprays can also include any of the conventional propellants to deliver the material as a foam, in the case of a mousse, or as a fine, uniform spray, in the case of an aerosol spray. Examples of suitable propellants include materials such as hydrofluorinated compounds, dichlorodifluoromethane, difluoroethane, dimethylether, isobutene, n-butane, propane, or trichlorofluromethane. A tonic or spray product having a low viscosity may also include an emulsifying agent. Examples of suitable emulsifying agents are anionic surfactants, cationic surfactants, nonionic surfactants, and mixtures thereof. Fluorosurfactants are especially preferred, particularly if the product is a preferred spray composition and most especially if it is a spray composition having a relatively low level of volatile organic solvents, such as alcohols, and relatively high levels of water (i.e., in excess of about 10 wt. %). If such an emulsifying agent is included, it is preferably present at a level of from about 0.01% to about 7.5% by weight of the composition. The level of propellant can be adjusted as desired, but is generally from about 3% to about 30% by weight of mousse compositions and from about 15% to about 50% by weight of the aerosol spray compositions.

Suitable spray compositions are well known in the art and include conventional, non-aerosol pump sprays, i.e., "atomizers", aerosol containers or cans having propellant, as described above, and also pump aerosol containers utilizing compressed air as the propellant. Pump aerosol containers are disclosed, for example, in U.S. Pat. No. 4,077,441, issued to Olofsson on Mar. 7, 1978, and U.S. Pat. No. 4,850,517, issued to Ter Stege on Jul. 25, 1989, both incorporated herein by reference.

A wide variety of additional components can be employed in the topical cosmetic/dermatological compositions herein. The compositions of the present invention can comprise a safe and effective amount of a pharmaceutical additive or adjuvant. The phrase "safe and effective" connotes an amount of an active agent high enough to significantly or positively modify the condition to be treated, but low enough to avoid serious side effects (at a reasonable benefit/risk ratio) within the scope of sound medical judgment. A safe and effective amount of the pharmaceutical active agent will vary with the specific active species, the ability of the composition to be applied, the particular condition being treated, the age and physical condition of the patient being treated, the severity of the condition, the duration of the treatment, the nature of concurrent therapy, and like factors.

The subject cosmetic/dermatological compositions can contain various emulsifiers when formulated as emulsions. These emulsifiers are useful for emulsifying the various carrier components of the compositions herein. Suitable emulsifiers can include any of a wide variety of nonionic, cationic, anionic, and zwitterionic emulsifiers disclosed in the prior patents and other references. See McCutcheon's, *Detergents and Emulsifiers,* North American Edition (1986), published by Allured Publishing Corporation; U.S. Pat. No. 5,011,681, issued to Ciotti et al. on Apr. 30, 1991; U.S. Pat. No. 4,421,769, issued to Dixon et al. on Dec. 20, 1983; and U.S. Pat. No. 3,755,560 issued to Dickert et al. on Aug. 28, 1973. These four publications are incorporated herein by reference in their entirety.

Suitable emulsifier types include acyl lactates, alkyl phosphates, carboxylic acid copolymers, esters and ethers of glucose, esters of glycerin, esters of propylene glycol, esters of sorbitan anhydrides, esters of sorbitol, ethoxylated ethers, ethoxylated alcohols, fatty acid amides, fatty acid esters of polyethylene glycol, fatty esters of polypropylene glycol, polyoxyethylene fatty ether phosphates, soaps and mixtures thereof.

Preferred emulsifiers can include, but are not limited to, ceteareth-20, ceteth-10, cetyl phosphate, diethanolamine cetyl phosphate, glyceryl stearate, PEG-100 stearate, polyethylene glycol 20 sorbitan monolaurate, polyethylene glycol 5 soya sterol, polysorbate 60, polysorbate 80, potassium cetyl phosphate, PPG-2 methyl glucose ether distearate, steareth-20, and mixtures thereof.

Typically preferred among these emulsifiers which are useful in the compositions of the present inventions is PPG-2 isoceteth-20 acetate (described in U.S. Pat. No. 4,559,226, issued to Fogel et al.).

The subject cosmetic/dermatological compositions can also contain various emollients. Examples of suitable emollients include, but are not limited to, highly branched hydrocarbons, non-polar carboxylic acid and alcohol esters, volatile and non-volatile silicone oils, and mixtures thereof. See, U.S. Pat. No. 4,919,934, issued to Deckner et al. on Apr. 24, 1990, which is incorporated by reference in its entirety.

Typically preferred among these emollients which are useful in the compositions of the present inventions are one or more of the following: octyldodecyl neopentanoate and propylene glycol isoceteth-3 acetate.

A variety of additional components can be incorporated into the subject cosmetic/dermatological compositions. Non-limiting examples of these additional components include cationic polymers and thickeners, chelators, gums and thickeners, low pH thickening agents, and polymers for enhancing film-forming.

In summary, sunscreen compositions containing active UV-A and UV-B compounds, e.g., avobenzone (UV-A) and benzophenone-3 (UV-B) are used in this invention. Other UV filter actives that may be employed in the present inventive compositions include p-aminobenzoic acid (PABA), camphor benzalkonium methosulfate, homosalate, phenylbenzimidazole sulfonic acid, terephthalidene dicamphor sulfonic acid, benzylidene camphor sulfonic acid, octocrylene, polyacrylamidomethyl benzylidene camphor, ethylhexyl methoxycinnamate, PEG-25 PABA, isoamyl p-methoxycinnamate, ethylhexyl triazone, drometrizole trisiloxane, diethylhexyl butamido triazone, 4-methylbenzylidene camphor, 3-benzylidene camphor, ethylhexyl salicyate, ethylhexyl dimethyl PABA, benzophenone-4, benzophenone-5, methylene bis-benztriazolyl tetramethylbutylphenol, disodium phenyl dibenzimidazole tetrasulfonate, bis-ethylhexyloxyphenol methoxyphenol triazine, and polysilicone-15.

The invention will now be described with reference to the following examples.

Examples 1–4 describe typical sunscreen formulations with and without X-Tend™ 226 (2-phenylethyl benzoate) present therein. The results show that the presence of X-Tend™ 226 increases the SPF factor of the formulation.

EXAMPLE 1

Anhydrous Oil Sunscreen Composition

| Phase | Ingredients | % w/w |
|---|---|---|
| A | Ceraphyl 368 (Ethylhexyl Palmitate) | 5.00 |
| | Escalol 567 (Oxybenzone) | 3.00 |
| | Escalol 517 (Avobenzone) | 3.00 |
| | Ceraphyl 41 ($C_{12-15}$ Alkyl Lactate) | 20.00 |
| | X-TEND ™ 226 | 20.00 |
| | Escalol 597 (Octocrylene) | 1.50 |
| | Escalol 587 (Octisalate) | 5.00 |
| | Ceraphyl 55 | 6.00 |
| | Escalol 557 (Octinoxate) | 7.50 |
| | Ganex V-216 (PVP-Hexadecene Copolymer) | 3.00 |
| | Vitamin E Acetate (Tocopheryl Acetate) | .010 |
| B | Si Tec DM 1 Plus (Dimethicone) | 5.00 |
| | Si Tec PTM 200 | 3.00 |
| | Si Tec CM 040 | 17.70 |
| C | Liquapar Optima (Phenoxyethanol and Methylparaben And Isopropylparaben and isobutylparaben and Butylparaben) | 1.00 |
| | Suncare Fragrance RR 82895 | 0.20 |

Procedure:

Combine phase A ingredients, mix with moderate stir and heat at 70° C. until everything is melted. Start cooling the batch and add phase B below 50° C., mixing after each addition, until clear. At 40° C. add phase C ingredients and mix until clear. SPF=22.8.

EXAMPLE 2

Anhydrous Oil Sunscreen Composition (Control)

| Phase | Ingredients | % w/w |
|---|---|---|
| A | Ceraphyl 368 (Ethylhexyl Palmitate) | 5.00 |
| | Escalol 567 (Oxybenzone) | 3.00 |
| | Ceraphyl 55 (Tridecyl Neopentanoate) | 25.00 |

-continued

| Phase | Ingredients | % w/w |
|---|---|---|
| | Escalol 517 (Avobenzone) | 3.00 |
| | Ceraphyl 41 ($C_{12-15}$ Alkyl Lactate) | 20.00 |
| | Escalol 587 (Octisalate) | 5.00 |
| | Escalol 597 (Octocrylene) | 1.50 |
| | Escalol 557 (Octinoxate) | 7.50 |
| | Ganex V-216 (PVP-Hexadecene Copolymer) | 3.00 |
| | Vitamin E Acetate (Tocopheryl Acetate) | 0.10 |
| B | Si Tec DM 1 Plus (Dimethicone) | 5.00 |
| | Si Tec PTM 200 (Phenyl Trimethicone) | 3.00 |
| | Si Tec CM 040 (Cyclopenthasiloxane) | 17.70 |
| C | Liquapar Optima (Phenoxyethanol and Methylparaben and Isopropylparaben and Isobutylparaben and Butylparaben) | 1.00 |
| | Suncare Fragrance RR 82895 Ungerer | 0.20 |

Procedure:

Combine phase A ingredients, mix with moderate stirring and heat at 70° C. until everything is melted. Start cooling the batch and add phase B below 50° C., mixing after each addition until clear. At 40° C., add phase C ingredients and mix until clear. SPF=12.0.

EXAMPLE 3

O/W Emulsion Sunscreen Composition

| Phase | Ingredients | % w/w |
|---|---|---|
| A | DI water | 50.95 |
| | Stabilize QM | 0.50 |
| | Butylene glycol | 3.00 |
| | Disodium EDTA | 0.15 |
| B | Cerasynt 840 | 2.00 |
| | Cerasynt 945 | 2.50 |
| | Ceraphyl 368 | 5.00 |
| | Escalol 557 | 7.50 |
| | Escalol 567 | 3.00 |
| | Escalol 517 | 3.00 |
| | X-TEND ™ 226 | 20.00 |
| C | NaOH 10% | 1.40 |
| D | Liquapar PE | 1.00 |

Procedure:

Sprinkle Stabilize in water with mixing. Heat the phase A at 80° C. Maintain 85° C. for 45 minutes with mixing. After 45 minutes add the remaining ingredients in phase A. Separate combine phase B ingredients heat at 80° C., mix until melted. Add phase B into phase A under propeller with good mixing. Mix until uniform. Start cooling down the batch. At 70° C. add phase C (NOH 10% solution). At 40° C. add phase D ingredient and mix well. SPF=25.7.

EXAMPLE 4

O/W Emulsion Sunscreen Composition (Control)

| Phase | Ingredients | % w/w |
|---|---|---|
| A | DI water | 50.95 |
| | Stabilize QM | 0.50 |
| | Butylene glycol | 3.00 |
| | Disodium EDTA | 0.15 |
| B | Cerasynt 840 | 2.00 |
| | Cerasynt 945 | 2.50 |
| | Ceraphyl 368 | 5.00 |
| | Escalol 557 | 7.50 |
| | Escalol 567 | 3.00 |
| | Escalol 517 | 3.00 |
| | Ceraphyl 41 | 20.00 |
| C | NaOH 10% | 1.40 |
| D | Liquapar PE | 1.00 |

Procedure:

Sprinkle Stabilize in water with mixing. Heat the phase A at 80° C. Maintain 85° C. for 45 minutes with mixing. After 45 minutes add the remaining ingredients in phase A. Separate, combine phase B ingredients, heat at 80° C., mix until melted. Add phase B into phase A under propeller with good mixing. Mix until uniform. Start cooling down the batch. At 70° C. add phase C (NaOH 10% solution). At 40° C. add phase D ingredient and mix well. SPF=22.6.

While the invention has been described with particular reference to certain embodiments thereof, it will be understood that changes and modifications may be made which are within the skill of the art. Accordingly, it is intended to be bound only by the following claims.

What is claimed is:

1. A sunscreen composition which includes at least one UV-B active ingredient therein, optionally with a UV-A active, and 2-phenylethyl benzoate in an amount sufficient to boost the SPF rating of said composition.

2. A sunscreen composition according to claim 1 which is a substantially anhydrous oil composition.

3. A sunscreen composition according to claim 1 which is an oil-in-water or water-in-oil emulsion based composition.

4. A composition according to claim 1 wherein said 2-phenylethyl benzoate is present in an amount of 10–30% by weight of the composition.

5. A composition according to claim 1 wherein said UV-B ingredient is a cinnamate, salicylate, camphor or p-aminobenzoic acid.

6. A composition according to claim 1 which includes one or more of benzophenone-3, avobenzone, p-aminobenzoic acid (PABA), camphor benzalkonium methosulfate, homosalate, phenylbenzimidazole sulfonic acid, terephthalidene dicamphor sulfonic acid, benzylidene camphor sulfonic acid, octocrylene, polyacrylamidomethyl benzylidene camphor, ethylhexyl methoxycinnamate, PEG-25 PABA, isoamyl p-methoxycinnamate, ethylhexyl triazone, drometrizole trisiloxane, diethylhexyl butamido triazone, 4-methylbenzylidene camphor, 3-benzylidene camphor, ethylhexyl salicyate, ethylhexyl dimethyl PABA, benzophenone-4, benzophenone-5, methylene bis-benztriazolyl tetramethylbutylphenol, disodium phenyl dibenzimidazole tetrasulfonate, bis-ethylhexyloxyphenol methoxyphenol triazine, and polysilicone-15.

* * * * *